United States Patent [19]
Burry et al.

[11] 3,978,397
[45] Aug. 31, 1976

[54] APPARATUS FOR SENSING PARTICLES

[75] Inventors: Peter Edwin Burry, Radlett; Roger Harley Kennedy, London, both of England

[73] Assignee: National Research Development Corporation, London, England

[22] Filed: Dec. 6, 1974

[21] Appl. No.: 530,150

[30] Foreign Application Priority Data
Dec. 6, 1973  United Kingdom............... 56499/73
Apr. 26, 1974  United Kingdom............... 18379/74

[52] U.S. Cl. ............................... 324/33; 340/237 S; 73/23
[51] Int. Cl.² ................... G01N 27/00; G01N 31/00
[58] Field of Search ............. 324/33; 250/379, 381; 73/194 F, 28, 23; 340/237 S

[56] References Cited
UNITED STATES PATENTS
1,808,709  6/1931  Blake ................................... 324/33
2,786,144  3/1957  Weisz ................................... 324/33

Primary Examiner—John K. Corbin
Assistant Examiner—Rolf Hille
Attorney, Agent, or Firm—Oblon, Fisher, Spivak, McClelland & Maier

[57] ABSTRACT

Method and apparatus for sensing solid particles in a mass of gas, for instance for detecting smoke in air and thus acting as a fire alarm. The gas is ionized and the remaining ionization is then detected after a time delay during which the smoke particles capture a proportion of the created ions. The time delay may be created either by physically separating the ionizing source and the detector and causing the mass to move from one to the other, or by operating source and detector intermittently with a time gap between each ionization and the subsequent detection.

6 Claims, 2 Drawing Figures

APPARATUS FOR SENSING PARTICLES

This invention relates to the sensing of solid particles within a mass of gas, and in particular to smoke detection and smoke measuring apparatus, especially ionisation chamber smoke detectors.

Existing smoke measuring ionisation chambers operate by simultaneously carrying out three functions: ionising the air, allowing the ions to react with the smoke particles, and extracting the remaining ions with an electric field. A reading of the resulting ionisation current gives a practical indication of the density of the smoke within the mass of gas, and hence of the probability of fire nearby. The design of such a chamber is necessarily a compromise between the requirements of each of the separate functions already mentioned. A disadvantage of existing designs of ionisation chamber is that the electric field rapidly removes the ions from the chambers, allowing little time for interaction between the ions and any smoke particles in the chamber.

The present invention arises from realising the value of separating in time the operation of the ionising device and the reading of the ionisation current or other indication, to allow a finite residence time during which the smoke or other solid particles can capture ions from the gas.

The invention is defined by the claims at the end of this specification, and examples of the invention will now be described with reference to the accompanying drawings, in which:

Figure 1:
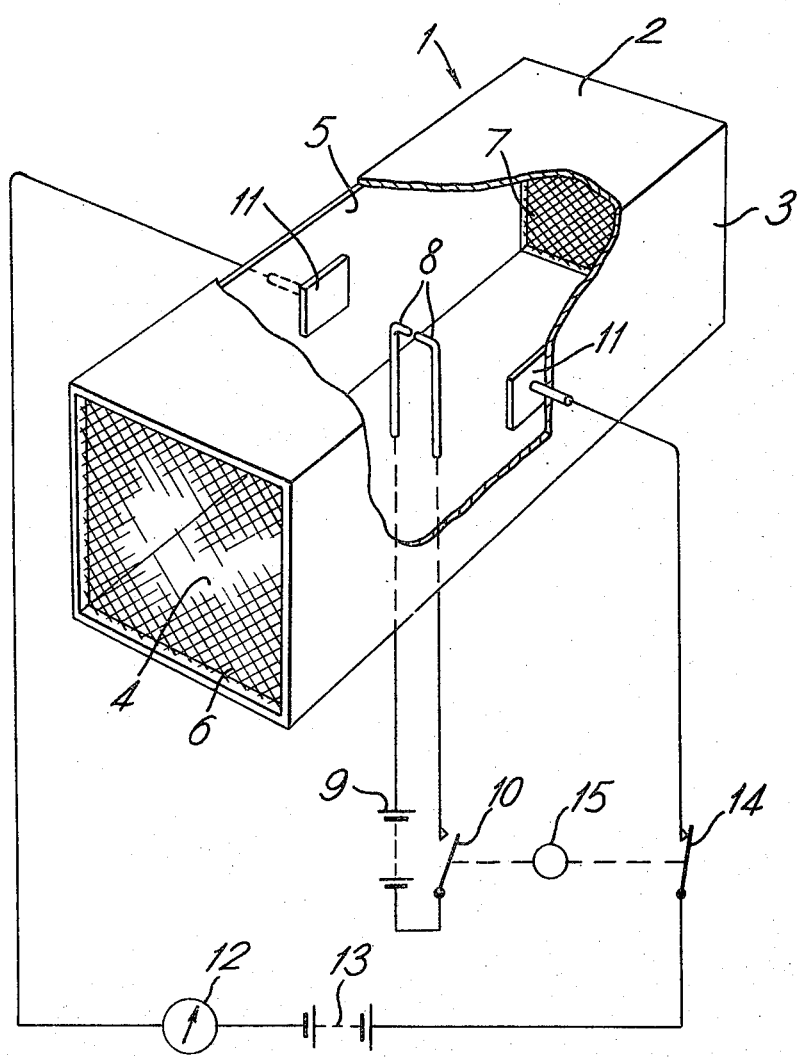
FIG. 1 is a diagrammatic perspective view of one apparatus.

FIG. 1 shows a rectangular chamber 1 with four long walls 2, 3, 4 and 5 and open ends covered by grills 6, 7 to keep out large airborne objects. In the middle of the chamber, mounted on the wall 4, are two electrodes 8, in circuit with a voltage source 9 and switch 10. Mounted on the inner faces of the walls 3 and 5 are detector system electrodes 11, in circuit with a current measuring device 12, a voltage source 13 and a switch 14. The switches 10 and 14 are linked by a cyclic control device 15 which ensures a sequence of operation in which switch 10 is first closed with 14 open, 10 then opens so that both switches are open for a period, 14 then closes for a period with 10 open, and the cycle then repeats. While electrodes 8 are energised, ionised air is produced within the chamber; in the succeeding delay period when switches 10 and 14 are both open, the ionisation of the air decays at a rate which is far greater if the air contains smoke particles than if it is uncontaminated; in the final period in which only switch 14 is closed, the total number of ions that reach the electrodes 11 will be higher for uncontaminated air than for smoky air, and the difference will be apparent from the reading of the current-measuring device 12.

Typically, the internal width, height and length of the chamber could each be 5cm, and the electrodes 8 could be of the needle-point type supplied by a short-pulsed 10kV source. Electrodes 11 could be metallic, separated by a distance of about 4cm and each with an area of about 10 sq. cm. Source 13 could be a 200V DC supply. Device 12 could include an alarm. It may be shown that the initial current across detector electrodes 11 is proportional to the function:

$$\left(\alpha t_r + \sqrt{\frac{\alpha}{q}}\right)^{-1}$$

where $\alpha$ is the recombination coefficient, $t_r$ is the delay period, and $q$ is the number of ion pairs generated per unit volume and unit time in the ionisation region. The above function was derived for a radioactive source. In a more general function applicable to other sources e.g. a corona discharge, the equivalent of $q$ would be a term proportional to the total number of ions generated per discharge cycle and dependent on other parameters, e.g. the dimensions of the chamber. Term $q$ is thus proportional to source strength, and it can be shown that if both $t_r$ and $q$ are large, then variations in $q$ will have little effect on the initial current. For normal smoke densities it can be shown that the ratio between the currents for clean and for smoky air, set up across electrodes 11 when switch 14 closes after the time delay, is given approximately by:

$$\frac{[\exp(\beta z \cdot t_r) - 1]}{\beta z \cdot t_r}$$

where $z$ is the number of smoke particles per unit of volume, $\beta$ is the mean capture coefficient of those particles for small ions, and $t_r$, as before, is the delay time. Useful results (governed by different formulae) could also sometimes be obtained by working the apparatus in a different mode in which switch 10 is operated cyclically as described above but switch 14 is always closed, so that the field of electrodes 11 is constant. The characteristics of the reading of device 12 will now of course be quite different before, and in particular the maximum value of the current that builds up and is recorded on the device will be lower than before because the electrodes 11 are removing ions from the air constantly. A key quantity now will be the time delay between the opening of switch 10 and the reading of device 12, rather than (as before) the period during which both of switches 10 and 14 are open.

Figure 2:
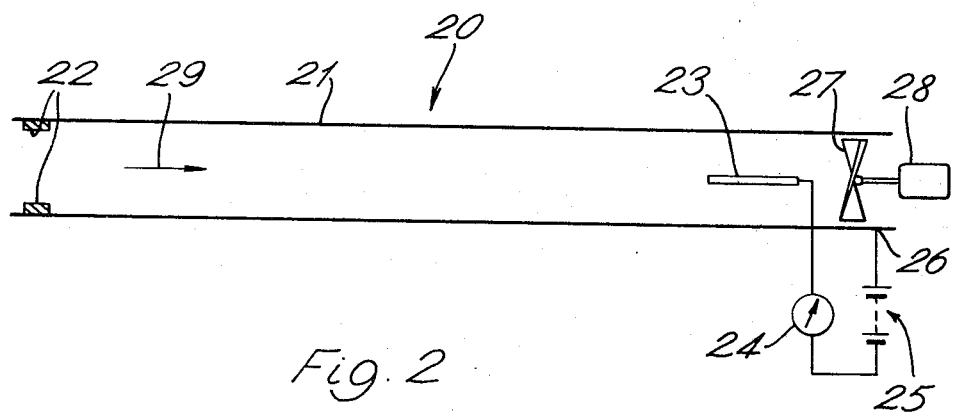
FIG. 2 is a more diagrammatic view of another apparatus.

The alternative apparatus of FIG. 2 comprises a long tubular chamber 20 with an electrically-conductive wall 21. Radiation sources 22 are mounted on the inner surface of wall 21 close to one end of the chamber, and an electrode 23 is mounted on the axis of the chamber close to the other end; this electrode is connected by way of a current measuring instrument 24 to a voltage source 25 which is grounded at 26 on wall 21. A fan 27, driven by motor 28, is mounted close to electrode 23 to draw masses of air down the chamber in the direction of arrow 29. Masses of air entering the chamber are ionised as they pass through the field of sources 22. They then pass down the middle of the length of the chamber under virtually zero electrical field conditions, and the time that they take for this travel constitutes a residence time during which smoke particles in the mass of air may capture some of the newly-created ions. The mass then reaches the field of electrode 23, and the voltage between this electrode and wall 21 is such that the uncaptured ions remaining in the mass of air are rapidly collected on either the wall or the electrode, giving a small ionisation current which may be read on instrument 24. The reading of this instrument will be relatively high in the normal case when the air flowing within chamber 20 is uncontaminated by smoke, and relatively low when smoke is present, the difference from normal giving some measure of the concentration of the smoke.

It has been pointed out that provided the ionising strength of the chosen source exceeds a certain level, variations in that strength may have little effect on the magnitude of the read-out of the apparatus, e.g. the current recorded by instruments 12 or 24. This opens the possibility of using as the source a radioactive isotope with a half-life comparable to the normal interval between maintenances of the apparatus. A suitable range of half-lives might be about 100 days – 2 or 3 years, and Polonium 210 or certain isotopes of Curium are proposed. One clear advantage of a short half-life, if the chosen source is radioactive, is that if the installation is unexpectedly reduced to rubble before the apparatus can be removed, then the radioactivity of the rubble will quickly decay.

We claim:

1. Apparatus for sensing the presence of solid particles within a gas comprising:
    a chamber to contain a mass of the gas;
    ionisation means to ionise the contained mass;
    detector means operable on the contained mass;
    time delay means, associated with the ionisation and detector means, to establish a substantially unvarying time interval between the exposure of each mass of gas to the ionisation means and its exposure to the detector means, and
    signal producing means associated with the detector means to yield a signal derived from the ionisation of the mass to indicate the concentration of solid particles within the gas.

2. Apparatus for sensing solid particles, according to claim 1, in which:
    said chamber is of elongated shape;
    said ionisation and detector means lie respectively towards opposite ends of said chamber;
    said time delay means includes an air movement device operable to cause said mass of gas as a whole to travel from the region of said ionisation means to that of said detector means within said chamber, whereby the travelling time between these small regions constitutes said time delay.

3. Apparatus for sensing solid particles, according to claim 1, in which:
    said ionisation and said detector means lie in proximity to each other within said chamber;
    said time delay means includes a switching device;
    said switching device is adapted to cause operation of said ionisation means and occurrence of said signal of said detector means to occur intermittently and alternately;
    said time delay comprises a finite time between the conclusion of each operation of said ionisation means and the occurrence of said succeeding signal of said detector means.

4. Apparatus for sensing solid particles, according to claim 3, in which said switching device causes intermittent and alternate operation of said ionisation and detector means, and said time delay comprises a finite time interval, during which both said means are inoperative, between each operation of said ionisation means and each succeeding operation of said detector means.

5. Apparatus for sensing solid particles, according to claim 3, in which said ionisation means is of a kind, for instance corona discharge or spark electrodes, which when energised gives rise to local electric fields to which said detector means is responsive.

6. Apparatus for sensing solid particles, according to claim 1, in which said ionisation means comprises radioactive material having a half-life of between about 100 days and 3 years.

* * * * *